(12) United States Patent
Braun et al.

(10) Patent No.: US 8,519,195 B2
(45) Date of Patent: Aug. 27, 2013

(54) PROCESS FOR THE MANUFACTURE OF ALKENONES

(75) Inventors: Max Braun, Wedemark (DE); Alain Lambert, Beauvechain (BE)

(73) Assignee: Solvay SA, Brussels (BE)

( * ) Notice: Subject to any disclaimer, the term of this patent is extended or adjusted under 35 U.S.C. 154(b) by 150 days.

(21) Appl. No.: 12/999,673

(22) PCT Filed: Jul. 6, 2009

(86) PCT No.: PCT/EP2009/058525
§ 371 (c)(1),
(2), (4) Date: Dec. 17, 2010

(87) PCT Pub. No.: WO2010/000871
PCT Pub. Date: Jan. 7, 2010

(65) Prior Publication Data
US 2011/0087052 A1   Apr. 14, 2011

(30) Foreign Application Priority Data

Jul. 4, 2008   (EP) .................................... 08159744

(51) Int. Cl.
*C07C 45/70* (2006.01)
*C07C 45/65* (2006.01)
*C07C 45/66* (2006.01)

(52) U.S. Cl.
USPC .......................................... 568/392; 568/404

(58) Field of Classification Search
USPC ................................................. 568/404, 392
See application file for complete search history.

(56) References Cited

U.S. PATENT DOCUMENTS

| 5,708,174 | A | 1/1998 | King et al. |
| 7,057,079 | B2 | 6/2006 | Braun et al. |
| 7,405,328 | B2 | 7/2008 | Hausmann et al. |
| 2010/0004457 | A1 | 1/2010 | Bland et al. |

FOREIGN PATENT DOCUMENTS

| EP | 0744400 A2 | 11/1996 |
| WO | WO 03066558 A2 | 8/2003 |
| WO | WO 2004108647 A2 | 1/2004 |
| WO | WO 2010037688 A1 | 4/2010 |
| WO | WO 2010099922 A1 | 9/2010 |
| WO | WO 2011003854 A1 | 1/2011 |
| WO | WO 2011003856 A1 | 1/2011 |
| WO | WO 2011003860 A1 | 1/2011 |

OTHER PUBLICATIONS

U.S. Appl. No. 13/120,505, filed Mar. 23, 2011, Braun.
U.S. Appl. No. 12/999,714, Braun, et al.
U.S. Appl. No. 12/999,730, Braun, et al.
U.S. Appl. No. 12/999,950, Braun, et al.
Tietze, L. F., et al—"Synthesis of Alkyl Propanoates by a Haloform Reaction of a Trichloro Ketone: Preparation of Ethyl 3,3-Diethoxypropanoate"; Organic Syntheses, 1990, vol. 69, p. 238-244; 7 pgs.
Colla, Agenor, et al—"Trihaloacetylated Enol Ethers—General Synthetic Procedure and Heterocyclic Ring Closure Reactions with Hydroxylamine" Synthesis, Issue 6, Georg Thieme Verlag, Stuttgart University, Jun. 1, 1991, pp. 483-486; 4 pgs.

*Primary Examiner* — Sikarl Witherspoon
(74) *Attorney, Agent, or Firm* — Beatrice C. Ortego

(57) ABSTRACT

Process for preparing an alkenone, which comprises (a) reacting a carboxylic acid halide with a vinyl ether by introducing vinyl ether into a liquid reaction medium containing carboxylic acid halide to form a halogenated precursor of the alkenone and (b) eliminating hydrogen halide from said precursor to form the alkenone.

19 Claims, No Drawings

PROCESS FOR THE MANUFACTURE OF ALKENONES

CROSS-REFERENCE TO RELATED APPLICATIONS

The present patent application is a U.S. national stage application under 35 U.S.C. §371 of International Application No. PCT/EP2009/058525 filed Jul. 6, 2009 which claims the benefit of the European patent application No. 08159744.5 filed on Jul. 4, 2008, the content of this application being incorporated herein by reference for all purposes.

The present invention relates to a process for preparing alkenone ethers.

Halogenated alkenone ethers, such as 4-ethoxy-1,1,1-trifluoro-3-butenone (ETFBO), are building blocks in chemical synthesis, as disclosed, for example, in U.S. Pat. No. 5,708,174. They may be prepared by reacting an acid chloride with a vinyl ether in the presence of a base, as described in the aforementioned U.S. patent. For this reaction, the base may also be used in excess as a solvent.

WO 03/066558 discloses production of alkenones from vinyl ethers and acid halides or acid anhydrides in the presence of onium salts. In the case of trifluoroacetic anhydride addition to ethyl vinyl ether, both addition of ethyl vinyl ether to a reaction medium containing trifluoroacetic anhydride and addition of trifluoroacetic anhydride to a reaction medium containing ethyl vinyl ether are described.

WO 2004/108647 discloses i.a. simplified production of alkenones comprising addition of carboxylic acid halides to vinyl ethers. In the examples, trifluoroacetyl chloride is added to ethyl vinyl ether.

It is an object of the present invention to provide an improved process for the preparation of alkenones, in particular concerning the selectivity and the yield of the production, whereby, amongst others, separation of the product can be simplified and loss of material and need for disposal of by-products can be reduced.

The invention concerns in consequence a process for preparing an alkenone, which comprises (a) reacting a carboxylic acid halide with a vinyl ether by introducing vinyl ether into a liquid reaction medium containing the carboxylic acid halide to form a halogenated precursor of the alkenone and (b) eliminating hydrogen halide from said precursor to form the alkenone.

The process according to the invention can advantageously be applied to preparation of an alkenone corresponding to Formula (I): R1—C(O)—C(H)=C(H)—OR2 (I) wherein R1 represents a C1-C10 alkyl group which is optionally substituted by at least one halogen atom or R1 represents CF3, CF2Cl, CF2H; and R2 represents aryl, substituted aryl, or a C1-C10 alkyl group which is optionally substituted by at least one halogen atom wherein an acid halide corresponding to Formula (II): R1—C(O)X (II) in which X represents fluorine, chlorine or bromine and R1 has the meaning given above, is reacted with a vinyl ether corresponding to Formula (III): CH2=C(H)—OR2 (III) in which R2 has the meaning given above.

R1 is often a fluorinated C1-C4 alkyl group. R1 preferably represents methyl, ethyl, n-propyl, isopropyl or methyl, ethyl, n-propyl or isopropyl substituted by at least one fluorine atom. It is especially preferred if R1 represents methyl, ethyl or methyl or ethyl substituted by at least one fluorine atom. CF3, CF2H, CF2Cl, C2F5, C3F7 are particularly preferred as R1. CF3, CF2Cl and CF2H are more particularly preferred as R1.

R2 can be selected for example from aryl, for example, phenyl, C1-C4 alkyl groups and/or phenyl substituted by halogen atoms. R2 is often a C1-C4 alkyl group. Preferably, R2 represents a linear or branched C1-C4 alkyl group, and particularly preferably R2 represents methyl, ethyl, n-propyl or isopropyl, most preferably a methyl or an ethyl group.

X is preferably selected from fluorine and chlorine, more preferably X is chlorine.

In a first particular embodiment, the carboxylic acid halide is trifluoroacetyl chloride.

In a second particular embodiment, the carboxylic acid halide is Chlorodifluoroacetyl chloride.

In a third particular embodiment, the carboxylic acid halide is Difluoroacetyl chloride.

In a forth particular embodiment, the carboxylic acid halide is trifluoroacetyl fluoride.

In a fifth particular embodiment, the carboxylic acid halide is (trifluoroaceto)acetyl fluoride.

In the process according to the invention and in the particular embodiments thereof, the liquid reaction medium generally contains at least 20% by weight of carboxylic acid halide relative to the total weight of the reaction medium. Preferably this content is at least 50% weight. In the process according to the invention and in the particular embodiments thereof, the liquid reaction medium may consist essentially of carboxylic acid halide. The liquid generally contains less than about 100% by weight of carboxylic acid halide, for example less than about 99% by weight to the total weight of the reaction medium.

In another aspect, the liquid reaction medium generally contains at least 1% by weight of carboxylic acid halide relative to the total weight of the reaction medium. Preferably this content is at least 5% weight. In this embodiment, the liquid generally contains less than about 20% by weight of carboxylic acid halide relative to the total weight of the reaction medium. Preferably this content is less than 10% weight. Preferably, the liquid contains 5 to 10% by weight of carboxylic acid halide relative to the total weight of the reaction medium. This particular aspect may also be applied to the different embodiments of the process according to the invention described herein. This particular aspect is especially advantageous when a solvent is used.

The reaction of step (a) or (b) can be carried out in the presence of a base. The base to be used may, for example, be a nitrogen-containing heterocyclic compound such as pyridine, quinoline or picoline; or a tertiary base such as triethylamine, dimethylaniline, diethylaniline or 4-dimethylaminopyridine. Among them, pyridine, triethylamine, dimethylaniline, diethylaniline or 4-dimethylaminopyridine is preferred. Among them, pyridine is particularly preferred. These bases may be used alone or in combination as a mixture. If appropriate, the base is used usually in an amount of from 1.0 to 3.0 equivalents, preferably from 1.05 to 1.5 equivalents, per mol carboxylic acid halide.

The reaction of step (a) or (b) can be carried out in the presence of an additional solvent. "additional solvent" is understood to denote a solvent different from the reactants and the products of said reaction. The solvent to be used may, for example, be an aromatic hydrocarbon such as benzene, toluene or xylene, an aliphatic hydrocarbon such as pentane or hexane; a halogenated hydrocarbon such as methylene chloride, chloroform or ethylene dichloride; or an ether such as diethyl ether, dibutyl ether or tetrahydrofuran. Among them, an aromatic hydrocarbon is preferred. Particularly preferred among them, is benzene or toluene. These solvents may be used alone or in combination as a mixture. If appropriate, the solvent is used usually in an amount of from 1 to 35 parts by weight, preferably from 3 to 16 parts by weight, per part by weight of the carboxylic acid halide.

The organic products of the reactions of step (a) and (b) in particular the halogenated precursor of the alkenone and, preferably, the alkenone can also be used as solvents for the reaction of step (a) and/or (b).

The invention further relates to a process for preparing a halogenated precursor of an alkenone, which comprises reacting a carboxylic acid halide with a vinyl ether in a liquid reaction medium comprising an alkenone or a halogenated precursor of the alkenone.

It has been found that alkenone, in particular ETFBO and halogenated precursor, in particular CETFBO (1,1,1-trifluoro-4-chloro-4-ethoxybutan-2-one) can be advantageously used as solvent for the reaction of the carboxylic acid halide with the vinyl ether.

In one embodiment, which is preferred, the liquid reaction medium for said reaction comprises an alkenone, in particular ETFBO. The alkenone is generally used in an amount of from 50 to 99% by weight, preferably from 60 to 99% by weight, more preferably from 75 to 99% by weight of the alkenone relative to the total weight of the reaction medium.

This embodiment is particularly advantageous for starting up said reaction.

The alkenone comprises preferably additional alkenone which is provided to the reaction from an external source, for example an earlier batch manufacture of alkenone. In one aspect of this embodiment, said reaction is carried out by introducing carboxylic acid halide into said alkenone containing liquid reaction medium, in particular during start-up of the manufacturing process. The formation of the halogenated precursor of the alkenone after introduction of a vinyl ether into the liquid reaction medium comprising the alkenone and the carboxylic acid halide will generally provide a liquid reaction medium containing the halogenated precursor and the alkenone.

It is understood that this embodiment may also be applied for reaction of the same type as reaction described above wherein the vinyl ether is not added to a reaction medium containing carboxylic acid halide, for example, vinyl ether may be dissolved in the alkenone containing reaction medium and carboxylic acid halide is then added to the reaction medium containing vinyl ether and alkenone.

In another embodiment, the liquid reaction medium for the reaction of the carboxylic acid halide with the vinyl ether comprises a halogenated precursor of the alkenone, in particular CETFBO. The halogenated precursor is generally used in an amount of from 50 to 99% by weight, preferably from 60 to 99% by weight, more preferably from 75 to 99% by weight of the halogenated precursor to the total weight of the reaction medium.

In a preferred aspect of this embodiment, the process is carried out in continuous mode. In a continuous process, the content of the halogenated precursor of the alkenone in the liquid reaction medium is generally kept in a range from 50 to 99%, preferably in a range from 60 to 99%, more preferably in a range from 75 to 99% by weight of halogenated precursor relative to the total weight of the reaction medium. This is particularly advantageous for a continuous process operated in steady-state, for example in a continuously stirred tank reactor (CSTR).

In a preferred aspect, the remainder of the liquid reaction medium comprises carboxylic acid halide.

In a sixth particular embodiment, which is preferred, the reaction of step (a) or (b) is carried out in the substantial or complete absence of a base, especially when a carboxylic acid chloride as described herein before is used.

In a seventh particular embodiment, which is preferred, the reaction of step (a) or (b) is carried out in the substantial or complete absence of additional solvent.

In a eighth particular embodiment, which is preferred, the reaction of step (a) or (b) is preferably carried out in the substantial or complete absence of base and of additional solvent, as described here before.

The sixth to eighth, in particular the eighth particular embodiment can be advantageously combined with any of the first to fifth particular embodiment.

In the sixth to eighth particular embodiments of the process according to the invention, "Substantial absence" typically denotes an optional content of equal to or less than 1% by weight, more particularly equal to or less than 0.5% by weight of base and/or solvent relative to the total weight of the reaction mixture. "Complete absence" in this context typically denotes a process wherein no voluntary addition of base and/or solvent to the reaction mixture has been carried out. Typically "complete absence" means that no base and/or solvent can be detected in a GC of the reaction mixture.

In particular the sixth to eighth particular embodiments of the process according to the invention allow for particularly efficient isolation of, if desired, the halogenated precursor of the alkenone and in particular the desired alkenone as reaction proceeds selectively and separation is facilitated by the limitation albeit substantial absence of components different from the starting material and the products of the reaction.

In the process according to the invention and in the particular embodiments thereof, the molar ratio of acid halide to vinyl ether preferably is from 0.8 to 1.2, and particularly preferably from 0.8:1 to about 1. Most preferably, the molar ratio is about 1.

In the process according to the invention and in the particular embodiments thereof, the vinyl ether is generally introduced into the liquid reaction medium at a rate of from 0.01 to 2 mol/hour/mol of carboxylic acid halide. Preferably this rate is from 0.5 to 1.5 mol/hour/mol of carboxylic acid halide. A rate of about 1 mol/hour/mol of carboxylic acid halide has given good results.

The process according to the invention and the particular embodiments thereof can be carried out batchwise or continuously In the process according to the invention and in the particular embodiments thereof, it is especially beneficial, in particular in a continuous process to control the concentration of the vinyl ether in the liquid reaction medium. Generally, this concentration is less than 5% by weight relative to the total weight of the liquid reaction medium. Often the concentration of the vinyl ether in the liquid reaction medium is equal to less than 1% by weight relative to the total weight of the liquid reaction medium. Preferably, this concentration is equal to less than 0.5% by weight relative to the total weight of the liquid reaction medium. Generally, this concentration is at least 0.1% by weight relative to the total weight of the liquid reaction medium.

It has been found that controlling the concentration of the vinyl ether avoids particularly the formation of other unwanted compounds such as chloroethers, polymeric materials and improves the yield and purity of the alkenone.

The invention concerns in consequence also a process for the manufacture of a halogenated precursor of an alkenone, which comprises reacting a carboxylic acid halide continuously with a vinyl ether in a liquid reaction medium wherein the concentration of the vinyl ether in the liquid reaction medium is controlled and preferably maintained in the ranges disclosed here before.

The invention also relates to a process for preparing a halogenated precursor of an alkenone, which comprises reacting a carboxylic acid halide with a vinyl ether in a liquid reaction medium and wherein the reaction medium is in turbulent state.

The process according to this specific embodiment, generally comprises carrying out the reaction at a temperature from 0° C. to 40° C., preferably from 10° C. to 30° C., more preferably at equal to or about 25° C. and most preferably at equal to or about 20° C.

In this specific embodiment, the turbulent state of the reaction medium can be achieved, for example, by an operation selected from stirring, passing the reaction medium through a flow resistance, mixing the reaction medium through introduction of gas bubbles such as an inert gas.

The stirring in the reaction medium may be realized by means of internal stirring such as a turbine or an agitator, or by means of a recirculation pipe exterior to the reactor.

Typical examples of a flow resistance are for example shaped bodies which can be placed in a reactor such as glass rings and Raschig rings.

In a particular aspect of this specific embodiment, which is particularly advantageous when the process is carried out in continuous mode, the vinyl ether and the carboxylic acid halide may be introduced into the liquid reaction medium through a concentric nozzle having an internal supply tube and an external supply tube. In this aspect, the vinyl ether is preferably supplied through the internal supply tube and the carboxylic acid halide is preferably supplied through the external supply tube.

It has been found, surprisingly, that by creating a turbulent state in the liquid reaction medium, hot spots can be substantially avoided in said reaction medium, thereby improving the yield and purity of the halogenated precursor of the alkenone and of the alkenone obtained from the precursor.

For the purpose of the present invention, the term "hot spot" denotes in particular a zone of the reaction medium having a substantially higher temperature than the temperature at which the reaction is carried out. "Substantially higher temperature" is understood a temperature which is at least 5° C., often at least 10° C. higher than the average temperature of the liquid reaction medium.

In the process according to this specific embodiment, the reaction is preferably carried out in a continuously stirred tank reactor (CSTR).

In a particular aspect said the continuously stirred tank reactor is combined with a plug flow reactor. In that case, generally, at least a part of the liquid reaction medium is withdrawn from the continuously stirred tank reactor and subjected to further reaction in a plug flow reactor. In this case, the CSTR reactor is usually in the turbulent state while the plug-flow reactor can be in turbulent or laminar flow state.

Particular embodiments of CSTR include reactors which consist of one or more cylindrical or spherical tanks wherein the turbulent state of the liquid reaction medium is created by any of the means described above. When more than one CSTR reactor is used, for example 2, 3 or 4 reactors, it is advantageous to split the feed of vinyl ether so as to feed vinyl ether to each reactor.

Particular embodiments of plug flow reactor are in the form of a cylindrical tube through which the feed enters at one end and exits at the other end.

The process according to the invention and in the particular embodiments thereof, preferably comprises carrying out the reaction of step (a) according to this specific embodiment.

The process according to the invention and the particular embodiments thereof, generally comprises carrying out the reaction of step (a) at a first temperature and carrying out step (b) at a second temperature higher than the first temperature.

The first temperature is generally less than 50° C., often less than 40° C., preferably equal to or less than 30° C. In one aspect, the temperature is preferably equal to or less than about −25° C. The first temperature is generally at least −50° C., often equal to or greater than −40° C., preferably equal to or greater than −30° C.

The second temperature is generally at least 50° C., often equal to or greater than 60° C., preferably equal to or greater than 70° C. The second temperature is generally less than 150° C., often less than 100° C., preferably equal to or less than about 80° C.

The process according to the invention and the particular embodiments thereof, generally comprises carrying out the reaction of step (a) at a first pressure and carrying out step (b) at a second pressure lower than the first pressure.

The first pressure is generally chosen to maintain the reaction medium in the liquid state. For example, if trifluoroacetyl chloride is used as acid halide, the first pressure is advantageously atmospheric pressure at a reaction temperature of equal to or less than about −25° C. The first pressure is advantageously a pressure equal to or greater than about 4, preferably about 5 bar abs to equal to or less than about 10 bar at a reaction temperature of from 20 to 30° C.

The second pressure is preferably chosen to allow for fractional distillation at least of the alkenone from the reaction medium. A typical second pressure is from 1 to about $10^{-3}$ bar abs In one embodiment of the process according to the invention and the particular embodiments thereof, which is advantageous when the process is carried out batch-wise, steps (a) and (b) are carried out in the same reaction zone, for example, a vessel surmounted by a distillation column.

In another embodiment of the process according to the invention and the particular embodiments thereof, which is advantageous when the process is carried out batch-wise, thereof step (a) is carried out in a first reaction zone and step (b) is carried out in a second reaction zone different from the first reaction zone.

The first reaction zone is often an optionally stirred tank reactor. The second reaction zone can be, for example, a distillation column.

In an ninth particular embodiment, which is preferred, the process according to the invention further comprises separating the alkenone produced in step (b) from hydrogen halide, unreacted carboxylic acid halide and unreacted halogenated precursor (and some traces of polymeric material) and optionally recycling carboxylic acid halide to step (a) and halogenated precursor to step (b).

A distillation, in particular a fractional distillation, is preferred as separation technique to separate the alkenone, in particular from the reaction mixture of step (b).

The invention further relates to a process for preparing an alkenone, which comprises the following steps:
  (a) providing a halogenated precursor of the alkenone, preferably by manufacture from a carboxylic acid halide and a vinyl ether in accordance with any of the processes disclosed herein before or a combination thereof
  (b) eliminating the hydrogen halide from said precursor to form the alkenone by a thermolysis treatment selected from a flash thermolysis, a vacuum thermolysis and a thermolysis under stripping with an inert gas.

For the purpose of the present invention, the term "flash thermolysis" refers to a process wherein the liquid reaction medium is heated up in a short time. Typical heating times for flash thermolysis are less than 1 hour, in particular less than 30 min, preferably about 15 minutes. Generally, the heating time is greater than 1 s, often greater than 15 s.

In particular aspects of the process according to this embodiment, the flash thermolysis is conducted at a temperature ranging from −20° C. to 140° C. and a period of time ranging from 30 seconds to 1 hour, preferably at a temperature ranging from 0° C. to 130° C. and a period of time ranging from 30 seconds to 30 min, more preferably at a temperature ranging from 20° C. to 120° C. and a period of time ranging from 30 seconds to 20 min.

The thermolysis or flash thermolysis can be optionally carried out under stripping with an inert gas stream such as nitrogen gas, argon gas.

For the purpose of the present invention, the term "stripping" denotes in particular a physical separation process where one or more components, in particular HCl, are removed from the liquid reaction medium by a gas stream. The liquid and gas streams can have concurrent or countercurrent flow directions.

If appropriate, the stripping is advantageously carried out with a nitrogen stream.

The process according to this embodiment, generally comprises carrying out the thermolysis at a temperature of −20° C. to 140° C., preferably from 60 to 130° C., for example at equal to or about 80° C. and more preferably at equal to or about 120° C.

The thermolysis or flash thermolysis may be carried out under vacuum. In that case, the vacuum is preferably from 100 to 600 mbar.

It is understood that the different processes and embodiments disclosed herein apply in most preferred way to the manufacture of chlorotrifluoroalkoxybutanone from alkylvinylether and trifluoroacetic acid halide, in particular from trifluoroacetyl chloride and ethyl vinyl ether and subsequent elimination to form trifluoroalkoxybutenone, in particular ETFBO.

It is understood that the different processes and embodiments disclosed herein apply in most preferred way to the manufacture of chlorodifluoroalkoxybutanone from alkyl-vinylether and difluoroacetic acid halide, in particular from difluoroacetyl chloride and ethyl vinyl ether and subsequent elimination to form difluoroalkoxybutenone, in particular EDFBO.

The examples here after are intended to illustrate the invention without however limiting it.

In these examples and throughout this specification the abbreviations employed are defined as follows: TFAC is trifluoroacetylchloride, EVE is ethyl vinyl ether, CETFBO is 4-Chloro-4-Ethoxy-1,1,1-trifluoro-3-butan-2-one, ETFBO is Ethoxy-1,1,1-trifluoro-3-buten-2-one.

EXAMPLE

Two-Step Manufacture of
4-Ethoxy-1,1,1-trifluoro-3-buten-2-one

Step (a)

In a 100 ml three-necked flask surmounted by a dry-ice cooler, equipped with a Pt100 internal thermometer 66.24 g (0.5 mole) trifluoroacetylchloride was condensed in at −30° C. 36.06 g (0.5 mole) of ethyl vinyl ether was added dropwise over 1 hour. After the addition, further 0.5 mole trifluoroacetylchloride was added. GC of a sample showed almost quantitative yield of 4-Chloro-4-Ethoxy-1,1,1-trifluoro-3-butan-2-one.

Step (b)

After the reaction of step (a) described above, the flask was warmed to room temperature and subjected to fractional distillation in vacuo. A first fraction (B.P. 59.3-66.4° C. at 47 mbar) contained a mixture of 4-Chloro-4-Ethoxy-1,1,1-trifluoro-3-butan-2-one and 4-Ethoxy-1,1,1-trifluoro-3-buten-2-one, which could be redistilled to provide further 4-Ethoxy-1,1,1-trifluoro-3-buten-2-one. A second fraction (B.P. 66.4-70° C. at 30 mbar) contained pure Ethoxy-1,1,1-trifluoro-3-buten-2-one (E/Z ratio 98.5:1.5). The isolated yield was 97.5% of theoretical yield.

EXAMPLE 2

Manufacture of 4-Chloro-4-Ethoxy-1,1,1-trifluoro-3-butan-2-one and 4-Ethoxy-1,1,1-trifluoro-3-buten-2-one under Turbulent Conditions and ETFBO as Solvent General procedure: Pure ETFBO, obtained by a previous synthesis, was placed into the flow part of a recirculation system and cooled using a chiller. This recirculation system comprises a 20 L flask, 2 one meter distillation columns filled with 10 mm glass Raschig rings placed on top of another distillation column, a circulation pump (1500 l/h), 3 tube reactors each with 3 m path length (diameter 1.5 cm). Once the desired temperature was reached in the recirculation system, gaseous or liquid trifluoroacetylchloride (15 kg/h; 113.2 mol/h) was introduced in the turbulent circulation in front of the first 3 m reactor and then a small molar excess of ethyl vinyl ether (TFAC/EVE =1:1.01) was added after the first 3 m reactor. The level in the 20 L flask of the recycle apparatus was kept constant by pumping material using a membrane pump into a second apparatus. This second apparatus which serves for the thermolysis of 4-Chloro-4-Ethoxy-1,1,1-trifluoro-3-butan-2-one (CETFBO) to 4-Ethoxy-1,1,1-trifluoro-3-buten-2-one (ETFBO), comprises a 100 L Pfaudler ceramic vessel with 3 one meter distillation columns filled with 10 mm glass Raschig rings and a cooler with removal. The conversion of CETFBO to ETFBO under loss of HCl takes place either through batchwise thermolysis when the ceramic vessel is full or through continuous feeding of the CETFBO stream from the recycle apparatus. The fine distillation was further carried out continuously or batchwise in the distillation columns.

EXAMPLE 2a

The recirculation system was filled with pure ETFBO and cooled to a temperature of 10° C. Following the general procedure, TFAC and EVE were introduced at a rate of 12.4 mol/h and 12.8 mol/h, respectively. A GC sample taken every hour at the top of the recycle apparatus, showed a complete reaction from TFAC with EVE whereby the CETFBO concentration was increasing continuously with a decreasing of the ETFBO concentration. The continuous introduction of TFAC and EVE was carried out during 8 hours and all the material was collected in the ceramic vessel. The thermolysis was carried out at 80° C. under a nitrogen stream, followed by a fractional distillation to provide 4-Ethoxy-1,1,1-trifluoro-3-buten-2-one in an isolated yield of 87% of the theoretical yield and with a purity (cis+trans isomer) of 98%.

EXAMPLE 2b

The same procedure was followed as example 2a but the recirculation system was kept at a temperature of 20° C.

Ethoxy-1,1,1-trifluoro-3-buten-2-one was obtained in an isolated yield of 87% of the theoretical yield and with a purity (cis+trans isomer) of 98%.

EXAMPLE 3

Conversion of CETFBO to ETFBO by Thermolysis Treatment

General procedure: After the reaction of step (a), as described above in example 1, the flask, fitted with a reflux condenser, was heated to the desired temperature by using an oil bath. The thermolysis or flash thermolysis was performed under different conditions: at different temperatures, with or without an inert gas stream or under vacuum. The conversion of CETFBO to ETFBO was followed by GC analyses. When the composition of the reaction mixture remained constant, the resulting reaction mixture was further subjected to a distillation in vacuo (70° C., 20 mbar) to obtain Ethoxy-1,1,1-trifluoro-3-buten-2-one. The experimental data are summarized in Table 1. The thermolysis time refers to the time after which the composition of the reaction mixture remained constant.

TABLE 1

| Example | Conditions | Thermolyis time [min] | % wt of CETFBO | % wt of ETFBO (cis/trans) | Isolated yield of ETFBO (%) |
|---|---|---|---|---|---|
| 3a | 80° C. | 43 | 5.2 | 88.9/1.3 | 85.7 |
| 3b | 80° C./N$_2$ stream (24 l/h) | 80 | 0.3 | 97.6/1.6 | 91.5 |
| 3c | 80° C./vacuum (400 mbar) | 80 | 1.4 | 95.1/1.7 | 89.3 |
| 3d | 120° C. | 17 | 1.2 | 94.3/1.4 | 89.9 |
| 3e | flash thermolysis 120° C. | 13 | 1.0 | 94.9/1.5 | 93.0 |
| 3f | flash thermolysis 100° C. | 25 | 2.8 | 93.7/1.4 | 93.7 |

The % wt of CETFBO and % wt of ETFBO (cis/trans) were measured by GC analyses.

The invention claimed is:

1. A process for preparing an alkenone corresponding to Formula (I): R1—C(O)—C(H)=C(H)—OR2 (I) wherein R1 is a fluorinated C1-C4 alkyl group or a CF3C(O)CH2 group, wherein R2 represents aryl, substituted aryl, or a C1-C10 alkyl group which is optionally substituted by at least one halogen atom, said process comprising: (a) reacting a carboxylic acid halide with a vinyl ether by introducing vinyl ether into a liquid reaction medium containing the carboxylic acid halide to form a halogenated precursor of the alkenone; and (b) eliminating hydrogen halide from said precursor to form the alkenone,
   wherein said liquid reaction medium consists essentially of said carboxylic acid halide or comprises said carboxylic acid halide and a solvent;
   wherein said carboxylic acid halide corresponds to Formula (II): R1—C(O)X (II) in which X represents fluorine, chlorine, or bromine, and
   wherein said vinyl ether corresponds to Formula (III): CH2=C(H)—OR2 (III) in which R2 has the same meaning as for Formula (I).

2. The process according to claim 1, wherein R1 is a a CF3 group.

3. The process according to claim 1, wherein R2 is a C1-C4 alkyl group.

4. The process according to claim 1, wherein the carboxylic acid halide is trifluoroacetyl chloride.

5. The process according to claim 1, wherein the liquid reaction medium contains from 20% to less than about 100% by weight of said carboxylic acid halide.

6. The process according to claim 1, wherein the liquid reaction medium consists essentially of said carboxylic acid halide.

7. The process according to claim 1, wherein the liquid reaction medium contains from 1% to less than about 20% by weight of said carboxylic acid halide.

8. The process according to claim 1, wherein the vinyl ether is introduced into the liquid reaction medium at a rate of from 0.01 to 2 mol/hour/mol of said carboxylic acid halide.

9. The process according to claim 1, wherein the reaction of step (a) is carried out in the substantial absence of a base.

10. The process according to claim 1, comprising:
    carrying out the reaction of step (a) at a first temperature and carrying out step (b) at a second temperature higher than the first temperature.

11. The process according to claim 1, wherein step (a) is carried out in a first reaction zone, and step (b) is carried out in a second reaction zone different from the first reaction zone.

12. The process according to claim 11, wherein the first reaction zone is an optionally stirred tank reactor, and the second reaction zone is a distillation column.

13. The process according to claim 1, which is carried out batchwise.

14. The process according to claim 1, which is carried out continuously.

15. The process according to claim 1, further comprising:
    separating the alkenone produced in step (b) from hydrogen halide, unreacted carboxylic acid halide, and unreacted halogenated precursor; and optionally recycling carboxylic acid halide to step (a) and halogenated precursor to step (b).

16. The process according to claim 1, wherein the liquid reaction medium contains from 50% to less than about 100% by weight of said carboxylic acid halide.

17. The process according to claim 1, wherein the liquid reaction medium contains from 5% to less than about 20% by weight of said carboxylic acid halide.

18. The process according to claim 1, wherein R2 is a methyl or ethyl group.

19. The process according to claim 1, wherein the concentration of the vinyl ether in the liquid reaction medium is maintained at a concentration of less than 5% by weight relative to the total weight of the liquid reaction medium.

* * * * *